United States Patent [19]

Vitovec et al.

[11] Patent Number: 4,528,006
[45] Date of Patent: Jul. 9, 1985

[54] APPARATUS FOR THE CONTINUOUS DESUBLIMINATION OF VAPORS OF SUBLIMING SUBSTANCES

[75] Inventors: Jaroslav Vitovec; Jan Cermak; Jiri Smolik, all of Prague, Czechoslovakia

[73] Assignee: Czechoslovenska akademia ved, Prague, Czechoslovakia

[21] Appl. No.: 516,298

[22] Filed: Jul. 22, 1983

[30] Foreign Application Priority Data

Jul. 23, 1982 [CS] Czechoslovakia ............. 5614-82

[51] Int. Cl.$^3$ ............................................. B01D 51/00
[52] U.S. Cl. ........................................ 55/269; 422/244; 55/82; 55/358
[58] Field of Search .................. 55/82, 267–269, 55/358; 23/294; 422/244

[56] References Cited

U.S. PATENT DOCUMENTS 4,080,182 3/1978 Vitovec et al. ................. 55/269

Primary Examiner—Bernard Nozick

[57] ABSTRACT

A continuous, desublimination apparatus capable of operating at high flow rates. The apparatus works on the principle of reducing temperature of a vapor-gas mixture below the desublimination point. It has a heated jacket with inlets and outlets of gases in which a gas permeable wall is coaxially spaced. Said wall encloses a desublimination space with nozzles for atomizing an evaporable liquid and with a distributor of a vapor-gas mixture at the inlet. The space between said gas permeable wall and the inner jacket wall is divided into at least three vertically aligned sections, the volumes of which increase in the direction away from said inlet of the vapor-gas mixture. In operation, a vapor-gas mixture is cooled below the desublimination point by an atomized liquid. Simultaneous blowing of a secondary gas through said gas permeable wall protects the wall of said desublimination space from solid deposits. The solid condensate is recovered from the gas phase in a separator, gas given off during operation of the apparatus leaves the apparatus, and the solid product is discharged from the apparatus as by a conveyer.

2 Claims, 1 Drawing Figure

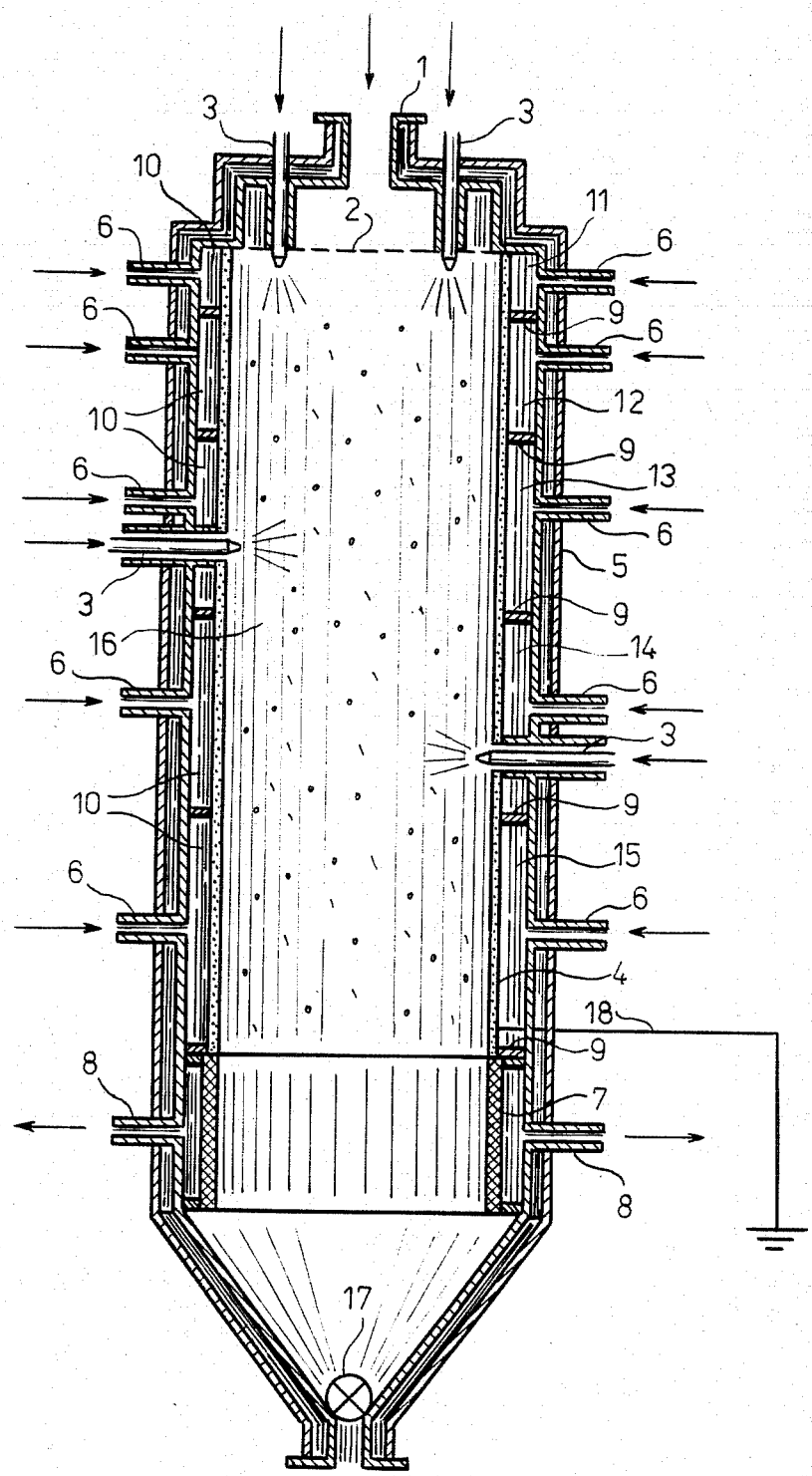

APPARATUS FOR THE CONTINUOUS DESUBLIMINATION OF VAPORS OF SUBLIMING SUBSTANCES

This invention relates to an apparatus for the continuous desublimation of vapors of subliming substances by reducing their temperature below the sublimation point, and provides novel equipment that can be operated effectively and reliably at high flow rates of the vapor mixture.

For the desublimation of the gaseous phase of sublimable substances, an apparatus is known (Czechoslovak Pat. No. 161,505), which comprises: a heated jacket with the heated inlet for a mixture; nozzles for the generation of a fine dispersion of a volatile liquid or water; tubes and inlets for a secondary gas, a filtering system for the withdrawal of non-condensed portion of the gas phase from the apparatus; a receptacle for accumulating the solid product; and a condensation space enclosed by a gas-permeable porous wall manufactured from a ceramic, glass or metal material, and situated inside the heated jacket.

This apparatus offers an advantage when compared with other apparatuses of the prior art. Such advantage is due to the fact that since the secondary gas is introduced into the desublimination space through the gas-permeable wall, no solid product can be deposited on the wall enclosing the desublimination space and, thus, no arduous operations are needed for removal of a layer of the product from this wall. However, expoeriments on the above prior apparatus with increased flow rates in the desublimation space showed that application of the apparatus described above is limited to the laminar region, i.e. when the Reynolds number, that is proportional to the flow rate of gas phase consisting of the gaseous mixture and secondary gas, is not larger than 2500. If the overall gas flow rate is increased, eddy motion and rapid mixing of the mixture occur. Due to this fact, the protective layer of a secondary gas at the gas permeable wall is disturbed, and the solid product is deposited on this wall. The build-up of a desublimation product on the wall makes it impossible to control the process and leads to the stoppage of desublimation.

Efforts to remove this drawback by a substantial increase of the flow rate of the secondary gas through the gas permeable wall result in the high consumption of a secondary gas, lowered efficiency of desublimation caused by dilution of the vapor-gas mixture, increased loss of the desublimation product in the gas leaving the apparatus, and in problems with protection of the environment. Turbulent flow of the gas mixture at atomizing nozzles for injection of the liquid brings about vapor condensation of subliming substances and the formation of solid deposits on the nozzles which adversely effect their function and lead to the stoppage of cooling of the mixture. Turbulent flow of the gas mixture also brings about a rapid motion of formed solid particles that become electrically charged. This fact creates a possible danger of explosion of the gas mixture in the apparatus. The two above-mentioned drawbacks could not be eliminated on the existing apparatus.

It has been found and verified by experiments that it is possible to work at flow rates corresponding to the turbulent flow on an apparatus in accordance with the invention for the continuous desublimation of vapors of subliming individual substances or from their mixture with inert gases by cooling below the desublimation point. Such apparatus includes a heated jacket with impermeable walls around the inner periphery of which at the same distance, in principle, a gas permeable wall is situated. The outer side of the gas permeable wall encloses, together with said inner wall of the heated jacket, a distribution space of a secondary gas medium said distribution space is equipped with inlets of said secondary gas medium and the inner surface of said gas permeable wall limits a desublimation space with inlets of a vapor-gas mixture and with nozzles for the atomizing of a vaporable liquid. The apparatus has a separator, connected to said desublimation space, for the removal of the non-condensed portion of the gas phase from the desublimation product, with outlets of the gas, a receptacle and conveyor of the desublimation product. Salient features of the present invention are that between said inlet of a vapor-gas mixture and said desublimation space, the distributor of the vapor-gas mixture is situated, said gas permeable wall is electrically conductive and is grounded, and said distribution space of a secondary gas is divided into at least three sections, which are disposed in a vertical row, with the aid of impermeable transverse partitions in such a way that the volumes of such sections increase with their distance from the inlet of the vapor-gas mixture.

In a rational, preferred design of the apparatus, the ratio of the volume of the first section to the volumes of the second, third, possible fourth and fifth vertical section is $1:4\pm 50\%$, $1:8\pm 50\%$, $1:12\pm 50\%$, and $1:20\pm 50\%$ respectively. The above-described sections are numbered starting at the inlet of a vapor-gas mixture.

The apparatus according to the invention permits working in the turbulent regime inside the desublimation space. Due to this feature, a substantially smaller apparatus, operating with lower consumptions of a secondary gas and of energy, and, therefore, working with reduced operating costs, is required for the same output. Tests with the apparatus of the invention showed that the desublimation product is more homogeneous in quality and that the separation of volatile impurities is better than in the apparatuses of the prior art. In the drawing:

a cross-section of a preferred embodiment of the apparatus of the invention is depicted schematically in the single IFIGURE.

The single FIGURE illustrates a preferred embodiment of the apparatus for continuous desublimation. The apparatus comprises a heated jacket 5 with an inlet of the vapor-gas mixture 1, a gas permeable wall 4 being coaxially situated within the jacket. The space bounded by the gas permeable wall 4 and an inner wall of the heated jacket 5 is divided by impermeable ring-like horizontal partitions 9 into five vertical sections, 11, 12, 13, 14 and 15, the volumes of which increase, in the direction from the upper inlet 1 of a vapor-gas mixture, in the ratios 1:4:8:12:20. A secondary gaseous medium is introduced through the inlet 6 to the individual sections 11, 12, 13, 14, and 15 of the distribution space 10. A desublimination space 16 is enclosed by the gas permeable wall 4. The vapor-gas mixture is introduced into space 16 through a distributor 2. Water is finely dispersed in the sublimation space by nozzles 3. The nozzles 3 are placed inside an insulation cover that narrows conically towards the mouth of the nozzles. Between the insulating cover and its sheath there is a space through which a secondary gas is blown. The desublimation space 16 is ended with the separator 7 and a gas inlet 8. The desublimed product is withdrawn from the apparatus by the paddle conveyer 17.

The gas permeable wall 4 is manufactured as a whole or in individual sections. It can be made as a wire basket with, at least, one layer of a gas permeable, usually glass, fabric. It can also be made of a porous metal material or manufactured as a supporting structure with at least one layer of a gas permeable fabric, provided that at least the upper layer is made of a fabric with woven-in electrically conductive fibers, or it is provided with a conductive coating. Electrically conductive parts of the apparatus which are in contact with the desublimation space 16 are grounded as shown by means of the supporting structure 18 of the gas permeable wall 4 on the heated jacket 5.

The apparatus according to this invention is operated as follows: A vapor-gas mixture introduced through the inlet 1 is distributed uniformly by the distributor 2 into the desublimation space 16. In the desublimation space 16, an evaporable liquid, water as a rule, is atomized by the nozzles 3. The vapor-gas mixture is cooled, by the evaporation of the liquid, below the desublimation point. In order to prevent an undesirable desublimation of solid substances on the walls of the desublimation space, a secondary gas is introduced through the gas permeable wall 4; the secondary gas does not allow the vapors to be in contact with the inner surface of the wall. The non-condensed portion of the vapor-gas mixture passes through the separator 7 and gas outlet 8. The solid product is accumulated at the bottom of the apparatus from where it is withdrawn by the conveyer 17.

Operation of the apparatus has been tested by desublimation of the vapors of anthraquinone, anthracene, naphthalene, phthalic anhydride and benzoic acid at throughputs of a vapor-gas mixture in the range of Reynolds number 5,000–40,000, which correspond to the transitional or turbulent flow. The velocity of a secondary gas, transpired gas through the gas permeable wall 4 in the first section 11, varied from 0.1 to 10 cm $s^{-1}$, in the second section 12 from 0.05 to 5 cm $s^{-1}$ and in the third section from 0.02 to 3 cm $s^{-1}$. When additional sections were included, the velocity of the secondary gas was gradually further reduced. The temperature of the transpired secondary gas depends upon the temperature of the vapor-gas mixture, and the concentration of the subliming substances, and can be 10–50 k lower than the temperature of the vapor-gas mixture. The temperature and velocity of the secondary gas usually decrease in the direction away from the inlet 1.

The apparatus according to this invention is designed for the desublimation of sublimable substances, and in combination with a sublimation unit for the purification of such substances.

Although the invention is described and illustrated with reference to a single preferred embodiment thereof, it is to be expressly understood that it is in no way limited to the disclosure of such preferred embodiment but is capable of numerous modifications within the scope of the appended claims.

We claim:

1. In an apparatus for the continuous desublimation of vapors of individual subliming compounds of from mixtures with inert gases by cooling below the desublimation point, said apparatus having a heated jacket with impermeable walls, a gas permeable wall disposed along the inner periphery of the jacket, the external side of said wall together with the inner wall of said jacket enclosing a distribution space provided with inlets of a secondary gaseous medium, the inner side of said gas permeable wall enclosing a desublimation space equipped with an inlet of a vapor-gas mixture and nozzles for the atomization of an evaporable liquid, a separator for the removal of a non-condensed gaseous phase from the product, and a gas outlet, the improvement wherein a distributor for the vapor-gas mixture is situated between the inlet of said vapor-gas mixture and the desublimation space, the gas permeable wall is electrically conductive and connected with all electrically conductive parts surrounding the desublimation space, the distribution space of the secondary gaseous medium is divided by impermeable partitions into at least three vertically aligned first, second and third sections of the distribution space, disposed respectively increasing distances from the inlet of the vapor-gas mixture, the volumes of said vertically aligned sections increasing with increasing distances of the sections from said inlet of the vapor-gas mixture, every individual section being provided with a separate inlet of the secondary gaseous medium.

2. An apparatus as claimed in claim 1, wherein a ratio of the volume of the first vertical section to that of the second, and to that of the third, possible fourth and a fifth is $1:4\pm50\%$, $1:8\pm50\%$, $1:12\pm50\%$, and $1:20\pm50\%$, respectively, the sections being numbered in the direction away from the inlet of a vapor-gas mixture, and means connecting to ground parts of the apparatus which are in contact with the desublimation space.

* * * * *